United States Patent [19]

Nakano et al.

[11] 4,013,364
[45] Mar. 22, 1977

[54] BASELINE CORRECTION IN DENSITOMETRICAL MEASUREMENTS

[75] Inventors: Kiyokazu Nakano; Hiroshi Yamamoto, both of Kyoto; Yasunori Ito, Otsu, all of Japan

[73] Assignee: Shimadzu Seisakusho Ltd., Kyoto, Japan

[22] Filed: Aug. 22, 1975

[21] Appl. No.: 607,085

[30] Foreign Application Priority Data

Aug. 29, 1974 Japan .............................. 49-99582

[52] U.S. Cl. .............................. 356/73; 250/557; 356/82; 356/96; 356/203
[51] Int. Cl.² ...................... G01N 21/00; G01J 3/36
[58] Field of Search ............... 356/73, 82, 96, 203; 250/559, 571

[56] References Cited

UNITED STATES PATENTS

| | | | |
|---|---|---|---|
| 3,768,913 | 10/1973 | Klimecki | 356/203 |
| 3,887,281 | 6/1975 | Kurita et al. | 356/203 |
| 3,924,948 | 12/1975 | Thoden et al. | 356/203 |

Primary Examiner—Vincent P. McGraw
Attorney, Agent, or Firm—Fidelman, Wolffe & Waldron

[57] ABSTRACT

Method and apparatus for densitometry wherein a sample spot developed on a supporting medium is scanned by monochromatic light in a zigzag way, and at a predetermined point outside the spot in each scanning stroke the measured output is periodically sampled and stored so as to be subtracted from the measured output during the scanning stroke for correction of the base line of the measured output.

16 Claims, 23 Drawing Figures

BASELINE CORRECTION IN DENSITOMETRICAL MEASUREMENTS

This invention relates to a method and an apparatus for densitometrical measurement of a sample such as spots developed on a support in thin layer chromatography, etc. by scanning the spots in a zigzag or reciprocal way with a beam of light. More particularly, this invention relates to a method and an apparatus for base line correction in such measurements.

Various methods have been proposed for quantitative determination of spots developed and separated on a thin plate or paper in thin-layer chromatography (TLC) or paper chromatography. For elmination of error or inaccuracy in measurement caused by the nonuniformity of the shape, size, position, or diffused condition of different spots, a method has been proposed by which a TLC spot is scanned in a zigzag way by a light beam having a small cross section as compared with the area of the spot and the light from the spot is detected to produce a corresponding signal, so that the profile of the density distribution of the substance contained in the spot is obtained or the quantity of the substance is determined by integrating the signal.

The zigzag scanning method has successfully solved the problems caused by the nonuniformity of the size, shape, position or diffused condition of the spots, but left unsolved those problems which are caused by the "background" such as the supporting plate itself or the solvent used for development of the spots. For example, if any impurity contained in the plate or the developing solvent is eluted during the develping operation to stain the background of the separated spots, fluctuation will occur in the base line of the measured output, with resulting introduction of errors into the measured values.

If there is no particular wavelength the substance under measurement absorbs, it is usually dyed with a suitable coloring agent, which sometimes unnecessarily dyes the background as well as the separated spots, so that the measured output includes a considerable part caused by the background, with resulting inaccuracy in the measurement.

Accordingly, the primary object of the invention is to provide a method of correcting the base line in a densitometer.

Another object of the invention is to provide a method of correcting the base line in a densitometer which varies or fluctuates in the direction in which the sample is developed.

Another object of the invention is to provide a method of correcting the base line in a densitometer of the type that scans a sample in a zigzag way by means of a thin beam of light.

Another object of the invention is to provide a method of eliminating from the measured output the background component caused by contamination of the TLC plate by impurities other than the sample components.

An other object of the invention is to provide a method of accurately measuring the spectrum of a spot developed on a TLC plate, etc. even when the absorption of the scanning light by the plate or the solvent itself varies with its wavelength to cause fluctuation to occur in the base line.

Another object of the invention is provide an apparatus for carrying out the method of the invention.

In one embodiment of the invention, a relative zigzag movement is caused to take place between the scanning beam and a sample under measurement. At a predetermined point outside a predetermined range in each stroke of the relative zigzag movement the measured value of the light from the background itself around a separated spot on the plate is sampled and held so as to serve as a base line for the measured output within the predetermined range in that or succeeding stroke of the zigzag movement. That is, the measured light value at a point outside the above-mentioned range in a stroke of the zigzag movement is substracted from the measured light value within the range in that or succeeding stroke of the zigzag movement, thereby compensating the measured output for any error caused by absorption by the background of the sample spot being measured.

By the method of the invention it is possible to compensate for fluctuations in the base line caused by the movement of the scanning light beam in the direction of the pitch of the zigzag scanning movement relative to the spot being scanned, and also fluctuations in the base line caused by wavelength scanning of the scanning light beam which is merely reciprocated across the spot without being moved in a zigzag way.

The invention will be described in detail below with reference to the accompanying drawings, wherein.

Figures 1A, 1B:
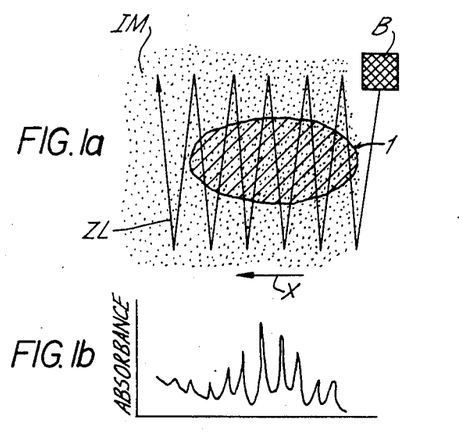
FIG. 1(a) schematically shows a prior art method of zigzag scanning of a spot on a TLC plate which has an appreciable background absorption of the scanning light.
FIG. 1(b) is a profile curve of the measured output obtained by the zigzag scanning of FIG. 1(a)
Figure 2A:
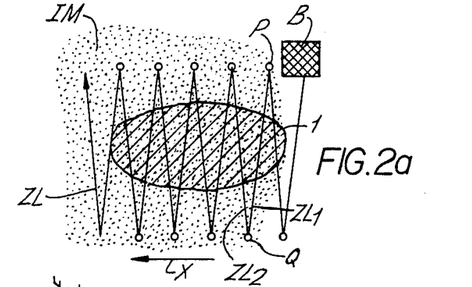
FIG. 2(a) schematically shows a zigzag scanning method of the invention conducted with base line correction on a spot similar to that of FIG. 1(a)

Now referring in detail to the drawings, first to FIGS. 1(a) and 2(a), there is schematically shown a spot 1 developed on a TLC plate. The plate is stained with an impurity shown as dusty dots IM the density distribution of which changes in the direction X, that is, in the direction in which the sample spot is developed or in the direction of the pitch of the zigzag scanning to be described below. If the spot is scanned by a light beam B along a zigzag locus ZL, an absorbance curve is obtained as shown in FIG. 1(b), with the base line fluctuating due to the uneven density distribution of the impurity in the background.

Figure 1C:
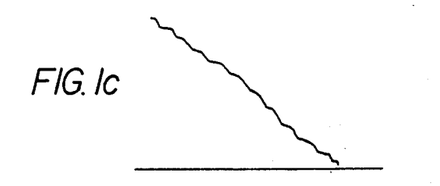
FIG. 1(c) is an integration curve of the measured output shown in FIG. 1(b)

If the curve shown in FIG. 1(b) is integrated, an integration curve as shown in FIG. 1(c) is obtained. The curve, however, neither shows the accurate quantitative determination of the spot, nor is it possible to know from the curve where the integration of the spot terminates.

In the drawing the cross section of the scanning beam and the pitch of the scanning movement are shown enlarged for the purpose of clear illustration. In practice the cross section of the beam is, for example, 1 mm × 1 mm, and the pitch is 1 mm.

In accordance with the invention, as shown in FIG. 2(a) at the end designated by a small circle of each stroke of the zigzag movement of the scanning beam, the measured output is sampled so as to serve as a new base line for the measured output, that is to say, the sampled value is substracted from the measured output, during the scanning stroke until the next sampling is conducted at the opposite end of the stroke. For example, the sample value at a point P is used as the base line for the measured output in the sanning stroke $ZL_1$ until a point Q is reached, whereupon a new output value is applied to serve as a new base line for the measured output in the next stroke ZL2 in place of the previous value sampled at the point P.

Each sampling point designated by the small circle is at the end of each stroke of the zigzag scanning and outside the spot 1, so that the measured value at the sampling point corresponds to the apparent absorbance at that point of the TLC plate, that is, the background absorbance of the plate. Therefore, if this sampled value is used as the base line level for the measured output during the ensuing stroke, the absorption by the background can be compensated for so as to render the quantitative determination of the substance contained in the spot the more accurate.

Figure 2B:
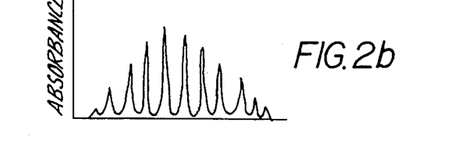
FIG. 2(b) is a profile curve of the measured output obtained by the zigzag scanning of FIG. 2(a)
Figure 2C:
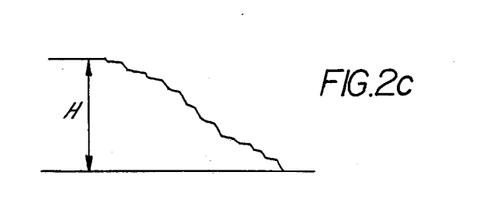
FIG. 2(c) is an integration curve of the measured output shown in FIG. 2(b)

FIG. 2(b) shows a profile curve and FIG. 2(c) shows an integration curve, both obtained by the base-line-corrected zigzag scanning of FIG. 2(a). The height H of the integration curve accurately shows the quantity of the substance contained in the spot that has been scanned.

In accordance with the invention, the base line fluctuation due to the variation or nouniformity of the optical characteristic of the supporting medium or background in the direction of development of the sample to be measured can thus be corrected by repeatedly sampling the measured output at a predetermined point outside the spot in each scanning stroke and correcting the measured output during the scanning stroke by the above-mentioned sampled output. By the output from the integrator it is also possible to know the termination of the integration of the spot.

Figure 10A:
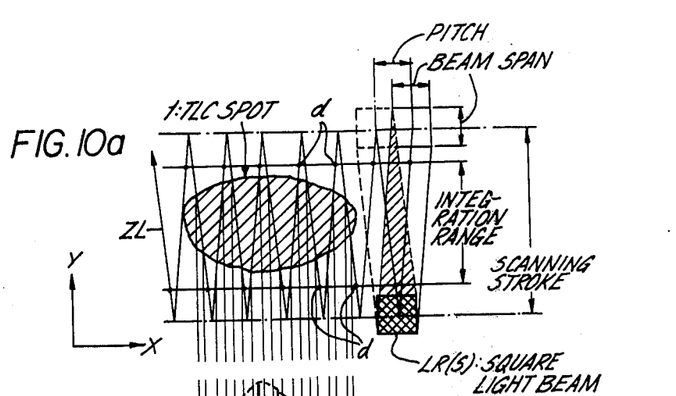
FIG. 10(a) illustrates the relation between the zigzag scanning of a TLC spot, the sampling of the base line output and the integration range of the measured output in the zigzag scanning method of the invention.

It should be noted that the sampling point need not necessarily be at the end of the stroke of the zigzag movement but that the point may be midway in the stroke provided that it is situated outside the spot, as will be described later with reference to FIG. 10. The sampling need not always be conducted in each and every stroke of the scanning but it may be conducted once every several scanning strokes provided that the pitch of the zigzag scanning is relatively small.

In this specification and claims the phrase "the light from the sample (or spot) or the supporting medium (or plate), etc." should be taken in a broad sense to mean not only the light transmitted through, or reflected or scattered by, the sample or the supporting medium, etc. but also the secondary light such as fluorescence or phosphorescence that is emitted by the excited sample or the supporting medium.

Figure 3:
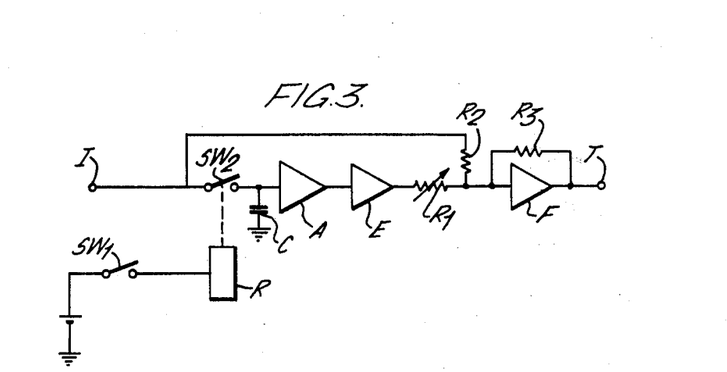
FIG. 3 is a schematic diagram of one embodiment of the base line correcting circuit constructed in accordance with the invention.

Turning to FIG. 3, the light from a TLC plate is converted by a photodetector to a corresponding electrical signal (to be referred to as the measured output). This output is converted to an absorbance signal to be applied to a terminal I. A switch SW1 is so arranged as to be closed by a sampling command signal produced by, for example, a pulse shaping circuit H to be described later with reference to FIG. 8 when a scanning head, not shown, has reached the end of each stroke of its zigzag scanning movement.

When the switch SW1 is closed, a relay R is energized to close a switch SW2. Since the scanning head stays at the end of the stroke only for a moment, the switch SW2 is closed also for a short period of time, which is negligibly short as compared with the cycle of the scanning movement, and during which time the absorbance signal obtained or sampled at the stroke end is charged into a capacitor C. While the scanning beam is in the course of the stroke, the switch SW2 is kept opened so that the capacitor holds the previously charged absorbance signal.

The signal held by the capacitor C is applied to a buffer amplifier A which has a high input impedance and a low output impedance. The output of the amplifier A is applied through a phase inverter E to an amplifier F. The amplifier F and resistors R1, and R2 and R3 constitute an adding circuit and produces at a terminal T an output corresponding to the sum of the absorbance signal directly sent from the input terminal I and the phase-inverted absorbance signal obtained at the stroke end and charged in the capacitor C, that is, an output corresponding to the absorbance value measured in the course of one stroke of the zigzag scanning movement minus the absorbance value sampled at the end of the previous stroke.

When the opposite end of the present stroke is reached, the switch SW2 is again closed, so that the absorbance value newly sampled at that end of the stroke is stored in the capacitor C to serve as the new base line for the succeeding stroke of the scanning movement.

The output at the terminal T is base-line-corrected as shown in FIG. 2(b). Integration of the output will give a correct quatitative determination of the spot.

It should be noted here that the term "scanning" in this specification and claims means not only the scanning of the whole area of a spot in a zigzag way but also the wavelength scanning, that is, to reciprocate a scanning light beam across the same area of the spot while changing the wavelength of the scanning light in each stroke of the reciprocation.

Figure 4A:
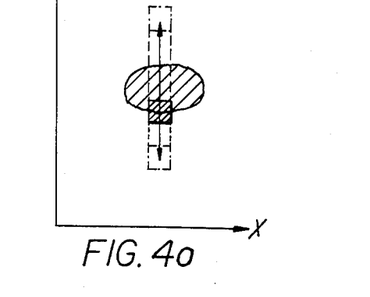
FIG. 4(a) schematically shows a method of reciprocal scanning of a TLC spot in the Y-direction alone, with the wavelength of the scanning light beam being changed in different strokes of the reciprocal movement of the light beam.
Figure 4B:
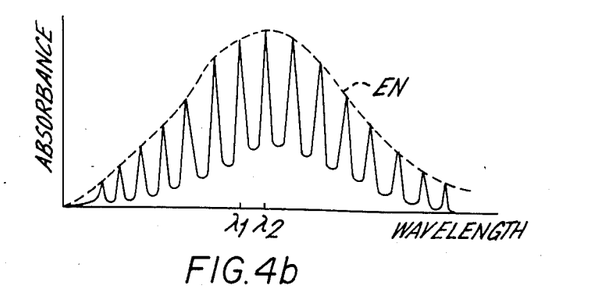
FIG. 4(b) shows a curve of the measured output obtained by the reciprocal scanning method of FIG. 4(a) without base line correction.
Figure 4C:
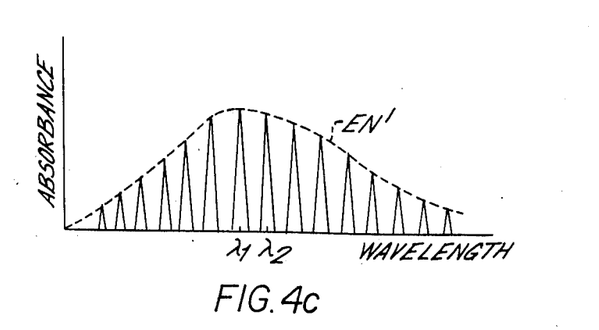
FIG. 4(c) is a curve similar to FIG. 4(b) but with the base line corrected in accordance with the invention.

In other words, the scanning is not restricted to the combination of the reciprocal movement of the scanning light beam and simultaneous feeding of the beam in the direction perpendicular to the reciprocal movement. If the reciprocal movement of the scanning beam is combined with simultaneous feeding thereof in the direction perpendicular to that of the reciprocation, the scanning light beam traces a zigzag locus across a TLC spot as shown in FIG. 2(a). However, if the scanning beam is only reciprocated without the above-mentioned simultaneous feeding thereof, the scanning beam traces a single straight locus traversing the TLC spot as shown in FIG. 4(a). In this case if the wavelength of the scanning light is changed in different scanning strokes, an absorbance curve as shown in FIG. 4(b) is obtained, in which an envelope EN connecting the peaks would express the absorption spectrum of the TLC spot. However, since the TLC plate itself or contaminant thereof has absorption or reflection characteristics varying with the wavelength of the scanning light, the base line fluctuates in FIG. 4(b), so that the envelope EN does not show the correct absorption spectrum of the spot. By compensating such base line fluctuations in accordance with the invention, it is possible to obtain an accurate absorption spectrum of the spot as shown at EN' in FIG. 4(c). In FIG. 4(b) the apparent maximum absorption is at $\lambda_2$, while in FIG. 4(c) the maximum absorption is at $\lambda_1$.

In the above embodiment, a new base line level is sampled at the end of each and every stroke of the scanning movement. The sampling may be made once every several scanning strokes, although this would require a more complicated mechanism than the illustrated arrangement that the sampling is conducted in each scanning stroke.

In the illustrated embodiment, the sampling is conducted at the opposite ends of the scanning stroke. It may also be conducted at only one end of the stroke provided that the TLC plate is substantially uniform widethwise (although this arrangement may involve a disadvantage that the nonuniformity widthwise of the TLC plate could not be averaged).

Figure 5:
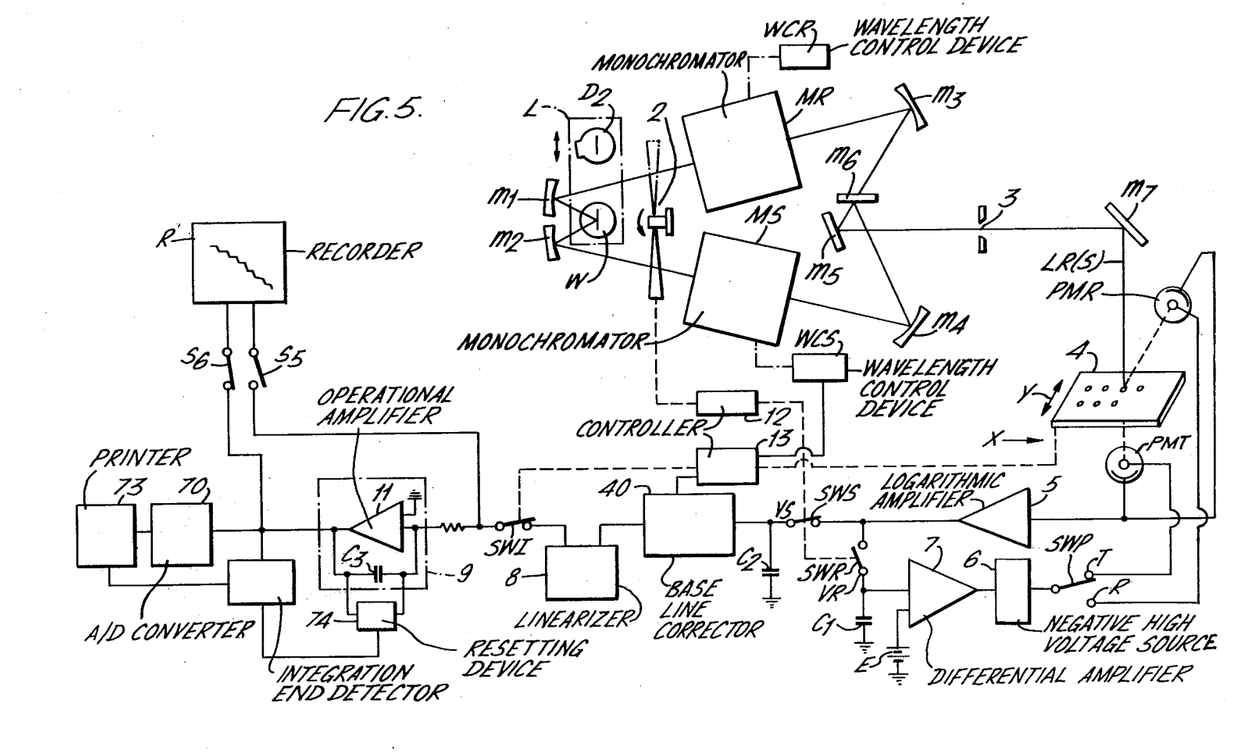
FIG. 5 shows a schematic diagram of a densitometer constructed in accordance with the invention.

FIG. 5 schematically shows a densitometer of the dual-wavelength zigzag scanning type which incorporates the base line correcting system of the invention. A light source L comprises a tungsten lamp W and a deuterium lamp D2, with a suitable switching device for effecting selective use of either one of the two lamps for the visible or ultraviolet region. The light from the source L is reflected by two collimating mirrors $m_1$ and $m_2$ so as to be introduced into two monochromators MR and MS, with a rotating chopper 2 alternatively intercepting the light entering the monochromators.

The monochromators produce two monochromatic light beams of different wavelengths $\lambda R$ and $\lambda S$, selected by wavelength control devices WCR and WCS, respectively. The two light beams reflected by concave mirrors $m_3$ and $m_4$, respectively, and caused by a half-mirror $m_6$ to alternately impinge on a plane mirror $m_5$ to be passed through a slit 3 and directed by a plane mirror $m_7$ onto a TLC plate 4 perpendicularly thereto.

The plate is moved at a predetermined constant speed relative to the beam linearly in the direction X longitudinal of the plate, that is, in the direction of development of the sample components. Simultaneously with this movement the plate is linearly reciprocally moved at a constant speed horizontally in the direction Y perpendicular to the above-mentioned direction X of movement. It will be easily understood that as the plate is moved in the above manner, it is scanned by the light beam in a zigzag way. The relative zigzag movement between the beam and the plate may be effected otherwise, for example, by reciprocating the light beam along the Y-axis while moving the plate linearly along the X-axis. A device for effecting the relative movement of the plate to the scanning beam will be described later with reference to FIGS. 6(a) to 6(d).

A photodetector PMT such as a photomultiplier tube detects the light transmitted through the plate 4, while another photodetector PMR detects the light reflected by the plate 4. The output terminals of the photomultiplier tubes are connected to the input of a logarithmic amplifier 5, the output of which is connected to a signal separating device such as a pair of switches SWS and SWR for taking out the outputs from the amplifier 5 caused by the sample and reference beams $\lambda S$ and $\lambda R$, respectively. To this end, the switches SWS and SWR are ganged with the chopper 2 through a suitable controller 12 so that when the chopper passes the light from the source to enter the monochromator MR while blocking it from the other monochromator MS, the switch SWR is closed and the switch SWS is opened, while when the chopper allows the light from the source to enter the monochromator MS while blocking it from the monochromator MR, the switch SWS is closed and the switch SWR is opened.

A capacitor Cl stores the reference beam signal VR when the switch SWR is closed, and a capacitor C2 stores the sample beam signal VS when the switch SWS is closed. The signal VR is also applied to a differential amplifier 7, to which a voltage source E provide a reference voltage. The output of the amplifier 7 controls a negative high voltage source 6 in such a manner that the difference input (VR - E) to the amplifier 7 becomes zero.

A switch SWP is provided to selectively actuate one of the photomultiplier tubes PMT and PMR. When the movable arm of the switch SWP is brought into contact with a terminal T, the photomultiplier tube PMT is energized to detect the light transmitted through the TLC plate 4, while when the arm is switched over to a terminal R, the photomultiplier tube PMR is energized to detect the light reflected by the plate.

When the switch SWS is closed, the absorbance signal or reflection absorbance signal from the logarithmic amplifier 5 is applied to the previously mentioned base line correcting circuit shown as a simple block 40 in FIG. 5. A controller 13 operates in association with the lateral reciprocal movement of the TLC plate 4 to control the operation of the base line corrector 40.

The base-line-corrected output from the circuit 40 is applied to a linearizer 8.

In densitometrical measurement of a spot developed on a TLC plate or like supporting medium, the scanning light is scattered by the supporting medium so that the measured absorbance value is not proportional to the concentration or quantity of the substance contained in the spot. The linearizer 8 is so arranged as to compensate the absorbance or reflection absorbance signal thereby to render the signal proportional to the true absorbance or reflection absorbance of the separated sample component in the TLC spot under measurement. For detailed explanation of the principle of operation and construction of the linearizer 8 reference should be made to a copending application.

A gate switch SWI is operated in a ganged relation to the lateral reciprocal movement of the TLC plate 4 so that within a predetermined range of the lateral reciprocation of the plate 4 the switch SWI is closed to transmit the output from the circuit 8 to a signal reading device R such as a recorder, indicator or printer directly or indirectly through an integrator 9.

Suppose that there are a plurality of spots developed on the plate side by side along the direction of lateral reciprocation or swinging of the light beam relative to the plate. The operation of the switch SWI is so controlled by the controller 13 that it is closed to pass the output from the circuit 8 caused by only a desired one of the spots. The integrator 9 includes an operational amplifier 11 and an impedance C3 for integration.

Figure 10B:
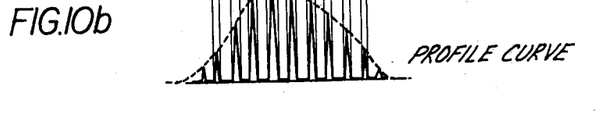
FIG. 10(b) is a profile curve obtained by the method of FIG. 10(a)
Figure 10C:
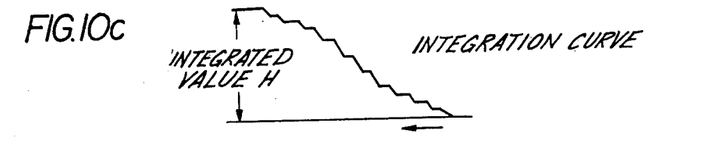
FIG. 10(c) is an integration curve obtained by the method of FIG. 10(a).

The recorder or indicator R records or indicates either the output from the linearizer 8 as shown in FIG. 2(b) or FIG. 10(b) directly or the integration output from the integrator 9 as shown in FIG. 2(a) or 10(c), or both of the outputs simultaneously.

The output from the integrator 9 is also applied to an A/D coverter 70 and an integration end detector 71 including a differentiator and a level detector. The output from the A/D converter 70 is applied to a printer 73. When the detector 71 has detected the end of the integration, that is, the integration curve in FIG. 2(c) or 10(c) having become horizontal, it produces an output to actuate the printer 73 to print out the integrated value received from the A/D converter. The output from the detector 71 is also applied to a resetting device 74 to reset the integrator 9 for the next integration.

FIGS. 6(a) to 6(d) show by way of example a mechanism for effecting relative movement between the plate 4 and the scanning beam LR or LS. The plate 4 is placed on a support 10, which is in turn mounted on a carriage 23 so as to be slidable relative thereto by means of rollers 28 in the direction of an arrow Y. To this end, an eccentric cam 24 fixed to the output shaft of a motor 26 mounted on the carriage 23 bears against a cam follower 25 attached to the support 10, with a spring 27 having its opposite ends fixed to the support 10 and the carriage 23 thereby biasing the support toward the cam. As the motor 26 rotates the cam 24, the support 10 is moved in the Y-direction on the carriage 23 by or against the force of the spring 27.

On the other hand, the carriage 23 is carried on a pair of guide rails 32 and 33 through the intermediary of rollers 29 and has at one side thereof a rack 34 which is engaged by a pinion 30 meshing with the output gear of a motor 31 secured to a machine frame, not shown. As the motor 31 rotates, the carriage 23 is moved on the rails 32 and 33 in the direction of an arrow X. If the movements in the X- and Y-directions are effected simultaneously a zigzag movement of the beam LR(S) relative to the plate 4 will result as shown in FIG. 2(a) or 10(a). If the movements in the X- and Y-directions are alternately effected, a modified zigzag movement of the beam relative to the plate will result. If the movement in the Y-direction alone is effected, the beam scans the spot reciprocally along a single straight locus as shown in FIG. 4(a).

Figure 6A:
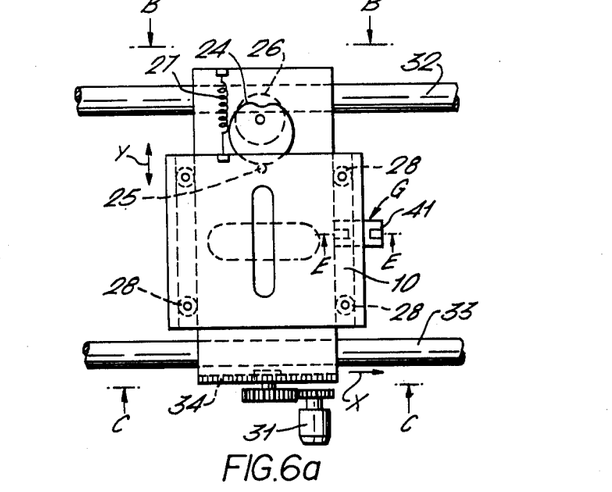
FIG. 6(a) is a top plan view of a mechanism for effecting the zigzag movement of a TLC plate relative to the scanning light beam, with a scanning beam position detector attached thereto.
Figure 6B:
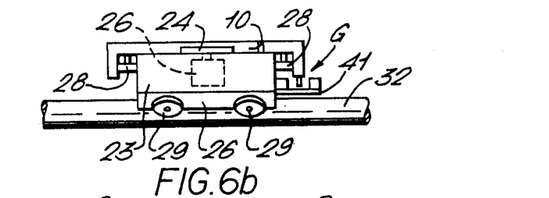
FIG. 6(b) is an elevational view as viewed in the direction of arrows B in FIG. 6(a)
Figures 6C, 6D:
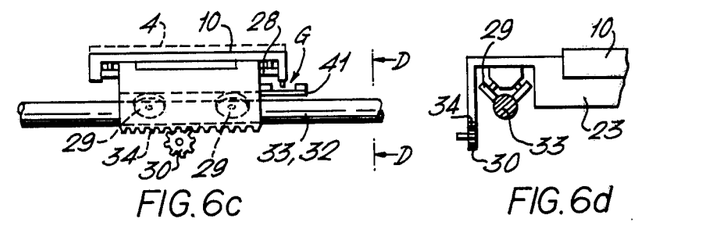
FIG. 6(c) is an elevational view as viewed in the direction of arrows C in FIG. 6(a)
FIG. 6(d) is a side elevation as viewed in the direction of arrows D in FIG. 6(c)

A scanning beam position detector G is provided in association with the above mechanism for effecting relative movement between the scanning beam and the plate 4. The device G detects the position of scanning light beam along the scanning locus thereof to produce a corresponding electrical signal.

Figure 7A:
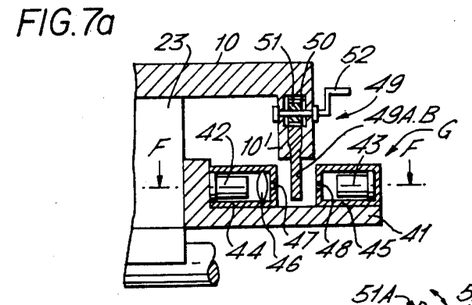
FIG. 7(a) is an enlarged vertical section taken along line E—E in FIG. 6(a), showing the detail of the scanning beam position detector.
Figure 7B:
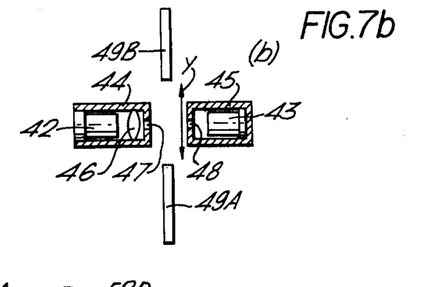
FIG. 7(b) is a sectional view taken along line F—F in FIG. 7(a)
Figure 7C:
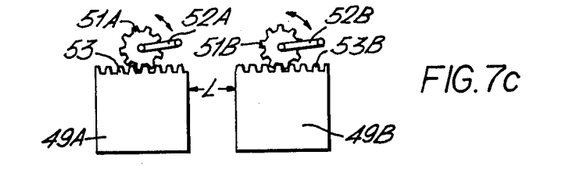
FIG. 7(c) is a side view of a portion of FIG. 7(a)

FIG. 7 shows one example of the concrete arrangement of the device G. A bracket 41 is secured to and projects laterally in the X-direction from the lateral side wall of the carriage 23 to support thereon a light source such as a luminescent diode 42 and a photodetector 43 such as a phototransistor in an opposed, spaced apart relation to each other. The diode 42 and the transistor 43 are enclosed in a shield covers 44 and 45, respectively, which are provided with a window 47, 48 in the opposed end walls thereof. The light from the diode 42 is converged by a lens 46 to pass through the windows 47 and 48 to hit the transistor 43.

A gating device 49 is provided in association with the light source 42 and the detector 43 to control the projection of the light from the source into the detector. The device 49 comprises a pair of intercepting plates 49A and 49B which are spaced a variable distance L apart from each other in the Y-direction and have their respective upper side portions slidably engaged in a guide groove 50 formed in a lateral skirt 10' depending from the support 10 of the mechanism shown in FIGS. 6(a) – 6(d).

On the upper edge of each of the intercepting plates 49A and 49B there is formed a rack 53A, 53B which meshes with a pinion 51A, 51B provided in the skirt of the support 10. A handle 52A, 52B is secured to the pinion 51A, 51B to manually rotate either or both of the pinions to move the intercepting plates 49A and 49B along the groove 50 in the direction perpendicular to the drawing sheet in FIG. 7(a) or in the Y-direction in FIG. 7(b) thereby to change the positions of the intercepting plates relative to the support 10 and the distance L between the two plates.

As the support 10 reciprocates in the Y-direction along the carriage 23 as previously mentioned, the intercepting plates 49A and 49B on the support 10 move in the Y-direction relative to the light source 42 and the photodetector 43 secured to the carriage 23. When the plate 49A or 49B comes between the light source 42 and the detector 43, the plate intercepts the light from the source 42 that has until then been incident on the photodetector 43. When the support 10 turns back at the end of the stroke of the lateral reciprocation thereof and moves in the opposite direction, the plate 49A or 49B that has been intercepting the light from the source 42 moves out of the optical path thereby permitting the light again to enter the photodetector 43.

Figure 8:
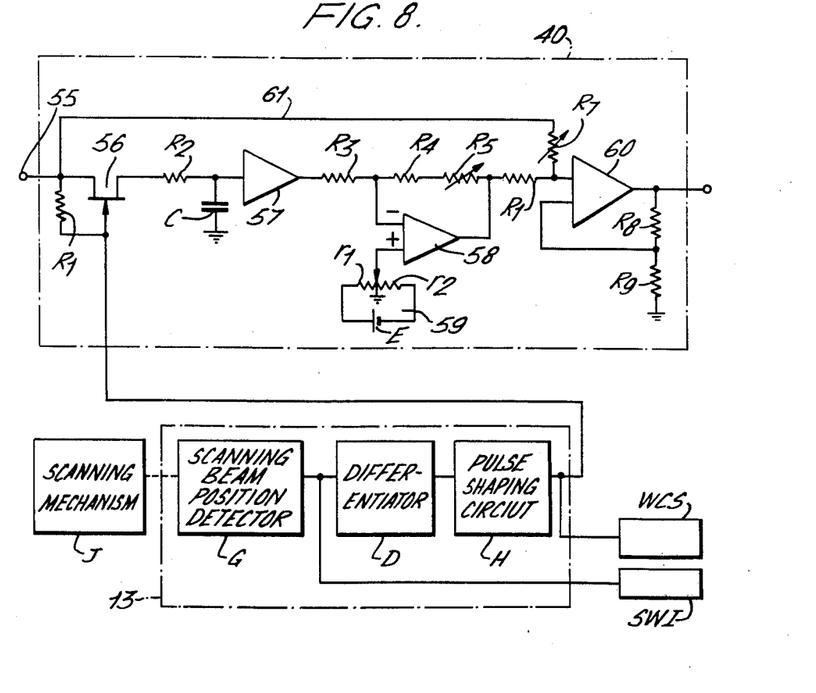
FIG. 8 is a schematic block diagram of another embodiment of the base line correcting circuit of the invention.
Figure 9:
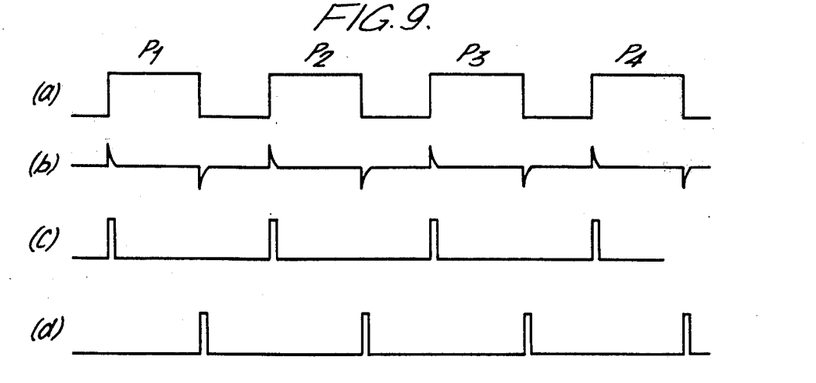
FIG. 9 shows waveforms for explanation of the operation of the sampling command signal producing circuit included in FIG. 8.

It will be easily seen that by changing the position of the plate 49A or 49B or both and/or the distance L therebetween it is possible to change the length and/or position of that range in one stroke of the zigzag or merely reciprocal movement of the scanning beam relative to the TLC plate in which the photodetector 43 detects the light from the source 42 to produce an output signal as shown in FIG. 9(a). This output is used in the manner to be described hereinafter with reference to FIGS. 8 and 9.

FIG. 8 shows another embodiment of the base line corrector of the invention. A scanning beam position detector G such as shown in FIGS. 7(a) to 7(c) operates in association with a scanning mechanism J such as shown in FIGS. 6(a) to 6(d) to produce a square wave output as shown in FIG. 9(a) for each one stroke of the scanning movement of the beam across a spot on the plate 4. To put it in detail, while the opening (or the detection range) between the interceptor plates 49A and 49B allows the light from the source 42 to pass through the opening to enter the photodetector 43 in each and every stroke of the scanning movement of the support 10, the photodetector 43 produces one square wave output shown in FIG. 9(a), and when toward the end of the stroke the plate, say, 49A intercepts the light beam from the source 42, the square wave output P1 terminates until the plate 49A turns back at the end of the stroke to move out of the light beam, thereby again to allow the beam to enter the photodetector, which produces the next square wave output P2.

The output from the scanning beam position detector G is applied to a differentiator D, which produces an output as shown in FIG. 9(b). A pulse shaping circuit H operates in response to either positive or negative differentiated output pulses from the differentiator D to produce output pulses having a predetermined height and width as shown in FIG. 9(c) or 9(d).

The absorbance signal the base line of which is to be corrected is applied to an input terminal 55. A sampling switch 56 such as a field effect transistor connected to the input terminal 55 operates in response to the sampling command signal as shown in FIG. 9(c) or 9(d) from the pulse shaping circuit so as to introduce the absorbance signal at the terminal 55 for the duration of the command signal into a capacitor C so that the signal is held therein to serve as a new base line for the absorbance signal reduced for the ensuing scanning stroke.

The charge time constant $t = CR2$ of the capacitor C is set to a negligibly small value as compared with the time T for one scanning stroke. For example, the charge time constant $t$ may be less than a few msec. if T is 100 msec.

To the capacitor C there is connected an impedance converter 57 having a high input impedance and a low output impedance, which can be a source follower amplifier employing a MOS field-effect transistor. A differential amplifier 58 has one input connected to the output from the amplifier 57 and the other input connected to an offset compensating voltage source 59 for elimination of offset. The source 59 is adjustable so that its output voltage is variable from a desired positive to a desired negative value.

An operation circuit 60 receives the absorbance signal directly from the terminal 55 through a line 61 and from the capacitor C the sampled base line value held therein and performs a required operation on the two inputs to make necessary base line correction for the measured absorbance signal. In the illustrated embodiment, the circuit 60 is so designed as to make addition, but with the connection of the two input terminals of the differential amplifier 58 being reversed, the circuit 60 may also be so designed as to make substraction.

The output of the scanning beam position detector G as shown in FIG. 9(a) can be used to repeatedly close the gate switch SWI for the period of time of duration of the output P1, P2, . . . for integration or direct recording of the output from the linearizer 8.

As previously mentioned, the pulse shaping circuit H may be so designed as to produce an output signal as shown either in FIG. 9(c) or (d) to be applied to the sampling switch 56. If the signal shown in FIG. 9(c) is used, the base line level sampled at the start of integration of the absorbance signal is used for base line correction during the period of the integration. If the signal shown in FIG. 9(d) is used, the base line level at the end of the previous integration period is used for base line correction during the next integration period. If the pitch of the zigzag scanning locus is relatively great, the result of measurement is more precise in the former than in the latter case.

The output pulse, either in the form of FIG. 9(b) or 9(c), from the pulse shaping circuit H is also applied to the wavelength control devices WCS for the monochromator MS so as to change the wavelength of the scanning beam LS as the beam reciprocally scans the spot as shown in FIG. 4(a).

Turning to FIG. 10(a), a TLC spot 1 is scanned by a light beam LR(S) having a square cross section along a zigzag locus ZL. The dot $d$ on each stroke of the scanning locus designates the point at which the base line level is sampled for base line correction during that scanning stroke and at which integration and/or direct recording of the output from the linearizer 8 is started.

If the output signal taken through the switch SWI as the zigzag scanning proceeds over the spot 1 is directly applied to the recorder R through the switch 85 having been closed, a base-line-corrected profile curve as shown in FIG. 10(b) will be drawn on the chart. If the output signal taken through the switch SWI is recorded through the integrator 9 with the switch S6 having been closed, an integration curve as shown in FIG. 10(c) will be obtained, which expresses the accurate quantity of the substance contained in the spot with the error due to the background absorption having been substantially eliminated therefrom.

By closing either or both of the switches S5 and S6, the two curves can selectively or simultaneously be recorded.

When the scanning of the spot has been completed, the detector 71 produces an output to actuate the printer 73 to print out the result of the integration and at the same time the resetting device 74 to reset the integrator 9.

What we claim is:

1. A method of densitometrical measurement of a sample spot developed on a supporting medium, comprising: scanning a predetermined area of said medium reciprocally along a single locus across said spot with light; changing the wave length of said scanning light with each stroke of reciprocation; measuring the intensity of the light from said scanned area to produce a corresponding electrical signal; periodically sampling said signal produced at a predetermined point outside said spot along said single locus each time said wavelength is changed; holding said sampled signal for a predetermined period of time; and correcting said signal produced during scanning of at least said spot before the next sampling by said sampled and held signal.

2. The method of claim 1, wherein said predetermined point is at the end of the stroke of said single locus.

3. The method of claim 1, wherein said light comprises a beam having a small cross section as compared with the area of said spot.

4. An apparatus for densitometrical measurement of a sample comprising: means for projecting monchromatic light onto a sample on a supporting medium; scanning means for repeatedly effecting a relative movement between said monochromatic light and said sample so that said monochromatic light scans along a continuous locus a predetermined area including at least a portion of said sample; means for detecting the intensity of the light from said scanned area to produce a first electrical signal corresponding to said intensity; means for periodically sampling the value of said first electrical signal produced when said light scans outside said sample; means for holding said sampled value for a predetermined period of time; correcting means for substracting said sampled and held value from said first signal produced by the scanning of at least said sample before the next sampling so as to produce a second electrical signal corresponding to the result of said substraction; and control means operable in response to the operation of said scanning means to control said sampling means and said correcting means.

5. The apparatus of claim 4, further including means operable in response to the operation of said control means to integrate the output of said correcting means.

6. The apparatus of claim 4, wherein said monochromatic light projecting means comprises a pair of monochromators each producing a monochromatic light beam of a different wavelength; and a chopper for causing said two monochromatic light beams to be alternately produced so that said two alternate monochromatic light beams pass along a common path to be projected onto said sample perpendicularly thereto.

7. The apparatus of claim 4, wherein said scanning means comprises first moving means for moving one of said light and said sample relative to the other in one direction along a first axis and second moving means for moving said first moving means reciprocally along a second axis perpendicular to said first axis, and wherein said control means includes position detecting means for detecting the position of said first moving means in its reciprocal movement along said second axis to produce a sampling command signal at a predetermined position of said first moving means and said sampling means includes means operable in response to said sampling command signal to temprarily store the level of said first electrical signal.

8. The apparatus of claim 4, wherein said scanning means comprises: means for supporting said sample supporting medium; carriage means on which said supporting means is carried for relative movement thereto; first drive means for moving said carriage means relative to said monochromatic light at a first constant speed linearly in one direction in a first plane perpendicular to the path of said monochromatic light; and second drive means for moving said supporting means at a second constant speed linearly and reciprocally in a second plane parallel with said first plane; and wherein said sampling means includes position detecting means comprising a light source and a photodetector for receiving the light therefrom, both carried on said carriage, and light projection control means carried on said supporting means for simultaneous movement therewith for controlling the projection of the light from said light source into said photodetector.

9. The apparatus of claim 8, wherein said position detecting means further includes means for adjusting the position of said light projection control means relative to said supporting means.

10. The apparatus of claim 4, further including means connected between said detecting means and said correcting means for converting said output signal from said detecting means to an absorbance or reflection absorbance signal.

11. The apparatus of claim 10, wherein said converting means comprises a logarithmic amplifier.

12. The apparatus of claim 1 wherein said control means further includes integrating means operable in response to the operation of said control means to integrate the output of said correcting means and wherein means are provided for causing said integrating means to operate within a predetermined range of said reciprocating movement of said one of said light and said sample along said second axis.

13. The apparatus of claim 5, further including means for reading the output from said integrating means.

14. The apparatus of claim 4, further including means for reading the output from said correcting means.

15. The apparatus of claim 4, further including means operable in response to said control means to control said monochromatic light projecting means so that the wavelength of said monochromatic light changes.

16. The apparatus of claim 6, further including means operable in response to said control means to control one of said monochromators so that the wavelength of the output monochromatic light therefrom changes.

* * * * *